United States Patent [19]
Margalit

[11] Patent Number: 5,480,612
[45] Date of Patent: Jan. 2, 1996

[54] KIT FOR DETECTING EXPLOSIVES

[75] Inventor: Yair Margalit, Rehovot, Israel

[73] Assignee: The State of Israel represented by the Prime Minister's Office, Israel Institute For Biological Research, Ness Ziona, Israel

[21] Appl. No.: 105,714

[22] Filed: Aug. 12, 1993

Related U.S. Application Data

[63] Continuation of Ser. No. 939,828, Sep. 3, 1992, Pat. No. 5,296,380.

[51] Int. Cl.[6] ................................................. G01N 37/00
[52] U.S. Cl. ............................ 422/61; 436/110; 436/111; 436/124
[58] Field of Search ..................... 422/61; 73/23.2; 436/110, 111, 124; 252/408.1, 301.6 R, 62.2; 423/395, 397, 264

[56] References Cited

U.S. PATENT DOCUMENTS

| | | | |
|---|---|---|---|
| 3,415,717 | 12/1968 | Avakian | 436/110 |
| 3,552,926 | 1/1971 | Fauth et al. | 436/110 |
| 3,817,705 | 6/1974 | Stein et al. | 436/110 |
| 4,690,902 | 9/1987 | Bitsch | 436/110 |
| 4,788,039 | 11/1988 | Glattstein | 436/110 |
| 5,157,261 | 10/1992 | Grey et al. | 436/110 |
| 5,296,380 | 3/1994 | Margalit | 436/106 |

FOREIGN PATENT DOCUMENTS

| | | | |
|---|---|---|---|
| 0264252 | 4/1988 | European Pat. Off. | 436/110 |
| 3235865 | 9/1988 | Japan | 436/110 |
| 1638619 | 3/1991 | U.S.S.R. | 436/110 |

OTHER PUBLICATIONS

Blatt, et al., *Organic Syntheses*, vol. I and II, pp. 90, 203, 211–213, 320, 418, 526, 580–581 (1948).
Almog, J., et al., *Journal of Energetic Materials* 4:159–167 (1986).
Baytos, J. F., Los Alamos National Laboratory, New Mexico, USA (1991) NTIS Publication #LA–12071–MS DE91 015321.

*Primary Examiner*—Laura Collins
*Attorney, Agent, or Firm*—Darby & Darby

[57] ABSTRACT

A kit for detecting nitroaromatic, organic nitrate, nitramine, inorganic nitrate, and chlorate and bromate explosives is characterized by the fact that for the detection of an inorganic nitrate, a reagent is used which comprises zinc powder suspended in a liquid comprising at least one water-miscible organic solvent, while for the detection of chlorates or bromates, a reagent is used which comprises an aniline salt in a homogeneous strongly acidic solution including at least one water-miscible organic solvent.

24 Claims, 1 Drawing Sheet

KIT FOR DETECTING EXPLOSIVES

This is a continuation of application Ser. No. 07/939,828, filed Sep. 3, 1992, now U.S. Pat. No. 5,296,380.

FIELD AND BACKGROUND OF THE INVENTION

The present invention relates to an improved method and kit for detecting explosives selected from nitroaromatics, organic nitrates (sometimes termed colloquially "nitroesters"), nitramines, inorganic nitrates, chlorates and bromates.

Particularly since what has become known as the Lockerbie incident, in which the undetected presence of explosive in an airplane resulted in tragic loss of life as well as material damage, an awareness of the need for rapid and reliable detection of explosives has become apparent. It is also evident that antiterrorist activity, more generally, will similarly make highly desirable, the availability of means for the ready detection of explosives. The present invention seeks to meet such needs, which are felt to an increasing extent at the present time.

An explosives detection kit marketed with the participation of the present assignees has proved highly successful commercially; see Almog. J. et al, J. Energetic Materials, 4: 159–167 (1986), who described a kit for detecting nitroaromatic, nitrate ester and nitramine explosives, the identification of inorganic nitrates being a later addition.

A "Field Spot-Test Kit for Explosives" using chemical reagents in a non-sequential procedure, as well as a portable ultraviolet lamp, has also been described (see Bayton, J. F., Los Alamos National Laboratory, N.M., USA, July 1991, NTIS publication #LA-12071-MS DE91 015321). However, this publication gives little or no indication of the sensitivity of the tests described therein. The disclosures of the above-stated literature articles are explicitly incorporated by reference herein.

In spite of the commercial success of a kit for detecting nitroaromatic, nitrate ester and nitramine explosives, based on the Almog et al model (above), this suffers from a number of drawbacks, which the present invention seeks to overcome, which drawbacks may be summarized as follows:

(1) two of the reagents are highly unstable to air and light, so that once the sealed ampoules containing them have been broken For test purposes, the kit has no reliable utility after 24 hours, and it is therefore discarded;

(2) one of the reagents is used in solid form, which, because of less reliable contact than a liquid, with a sample, makes a test utilizing it less reliable than is desirable;

(3) the existing kit does not detect chlorates, which are a possible ingredient of improvised explosives.

SUMMARY OF THE INVENTION

The present invention accordingly provides an improved method for detecting explosives selected from nitroaromatics, organic nitrates, nitramines, inorganic nitrates, chlorates and bromates, which method comprises a preliminary step of providing a sample from a suspect source, and at least the first of the following steps carried out in the stated sequence, namely:

(a) contacting the sample with a first reagent, which is an alkaline solution of sulfanilamide or an analogous aminoaromatic azo-dye precursor, whereby the presence of a nitroaromatic type explosive affords a distinct coloration; and in the absence of such coloration, (b) contacting the same sample, which is already in contact with the first reagent, with a second reagent containing a nitrate to nitrite ion reducing agent and a diazo-coupler which gives a highly-colored product on reaction with a diazonium compound formed by reaction of the sulfanilamide or an analogous aminoaromatic azo-dye precursor with nitrite ion, the second reagent being sufficiently strongly acidic so that it neutralizes and makes acidic a mixture thereof with an equal volume of the first reagent in contact with the suspect sample, whereby the presence of an organic nitrate or nitramine type explosive affords a distinct coloration; and in the absence of such coloration, (c) contacting the same sample, which is already in contact with the first and second reagents, with zinc powder suspended in liquid phase, whereby the presence of inorganic nitrate affords a distinct coloration; and in the absence of a distinct coloration in all of steps (a), (b) and (c), a second sample is provided From the same suspect source, and is submitted to step (d), namely:

(d) contacting the second sample with an aniline salt in a homogeneous strongly acidic solution including at least one water-miscible organic solvent, whereby the presence of chlorate or bromate affords a distinct coloration.

It is presently preferred that in the method of the invention, at least one of the following conditions (a'), (b'), (c'), (d') applies, namely:

(a') the first reagent contains as solvent at least one water-miscible alcohol and at least one other water-miscible organic compound;

(b') the diazo-coupler contains an aminonaphthyl moiety and the second reagent comprises aqueous oxyacid;

(c') the liquid phase comprises at least one water-miscible alcohol and at least one other water-miscible organic compound;

(d') the strongly acidic solution comprises an oxyacid and contains also at least one water-miscible alcohol and at least one other water-miscible organic compound.

In accordance with a particular embodiment of the method of the invention, at least one of the following conditions (a"), (b"), (c"), (d") applies, namely:

(a") the First reagent contains as solvent dimethyl sulfoxide (DMSO) and at least one alcohol selected from methyl alcohol and isopropyl alcohol;

(b") the diazo-coupler is N-(1-naphthyl)ethylenediamine and the second reagent comprises aqueous phosphoric acid and a reducing agent comprising hydrazine and a thiosulfate salt;

(c") the liquid phase comprises dimethyl sulfoxide (DMSO) and at least one alcohol selected from methyl alcohol and isopropyl alcohol;

(d") the strongly acidic solution comprises sulfuric acid and contains also DMSO and ethanol.

The present invention moreover provides a test kit for use in an improved method for detecting explosives selected from nitroaromatics, organic nitrates, nitramines, inorganic nitrates, chlorates and bromates, which kit comprises the following components, each of components (ii), (iii), (iv) and (v) being contained in respective dropwise dispensing means, namely:

(i) absorbent means for sampling a suspected source selected from a suspected substance, a surface of an inanimate object and the exterior periphery of a human;

(ii) alkaline solution of sulfanilamide or an analogous aminoaromatic azo-dye precursor;

(iii) a solution containing a nitrate to nitrite ion reducing agent and a diazo-coupler which gives a highly-colored product on reaction with a diazonium compound formed by reaction of sulfanilamide or an analogous aminoaromatic azo-dye precursor with nitrite ion, the solution being sufficiently strongly acidic so that it neutralizes and makes acidic a mixture thereof with an equal volume of the alkaline solution;

(iv) zinc powder admixed with liquid means which on shaking gives zinc powder suspended in liquid phase;

(v) an aniline salt in a homogeneous strongly acidic solution including at least one water-miscible organic solvent.

DETAILED DESCRIPTION OF THE INVENTION

Figure 1:
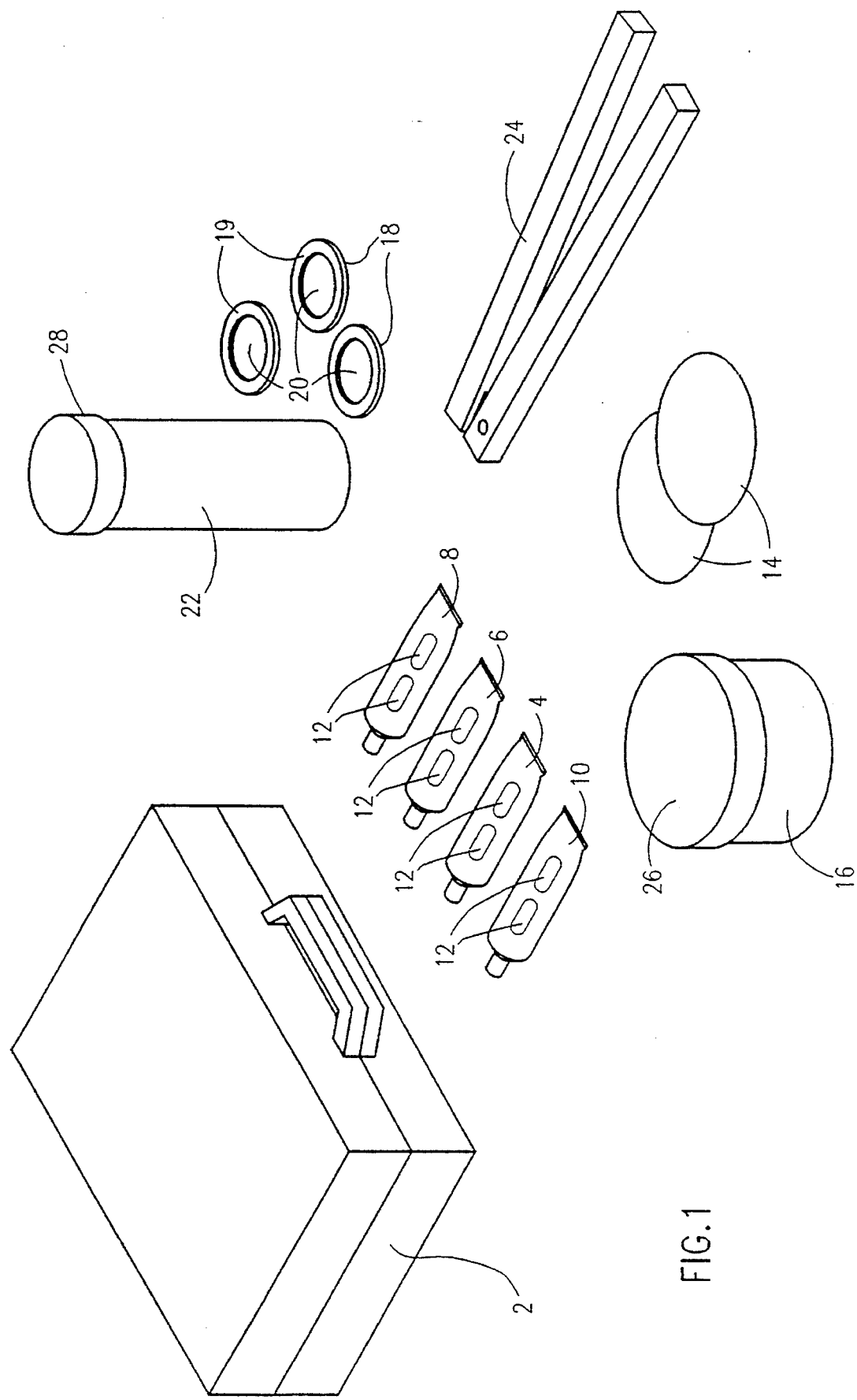
FIG. 1 depicts a particular embodiment of a kit in accordance with the present invention.

It will be apparent that at least one of the above-stated conditions (a'), (b'), (c'), (d'), as well as the above-stated conditions (a"), (b"), (c"), (d"), may be applied to the corresponding components in the kit of the invention. In a presently preferred embodiment of the kit of the invention, each of components (ii), (iii), (iv) and (v) are separately contained in sealed breakable ampoules which are in turn contained within corresponding closed plastic tubes adapted for dispensing each of the components in a dropwise manner. Also in a particular embodiment, at least the ampoules of components (ii) and (iii) contain additionally an inert gas such as argon to minimize deterioration of the chemical reagents which they contain.

In a presently preferred embodiment of the invention, preparation of the test reagents may be carried out as follows.

Preliminary notes: (1) Reagents A and B are extremely sensitive to air and light, so that stringent precautions must be taken in this regard, in the manner known to persons skilled in the art. For example, air is excluded by working in the presence of an inert gas such as nitrogen or argon, and all operations including mixing, filling of ampoules and so forth, are preferably conducted in a dim light, while storage vessels including ampoules, as well as the plastic tubes containing them in the kits according to embodiment of the invention, are darkly colored to prevent deterioration of the reagents in presence of light. The ampoules are desirably filled with an inert gas such as argon. (2) Dimethylsulfoxide (DMSO) has been used extensively in the preparation of the exemplified test reagents. Because this substance is a powerful solvent, it is believed to increase the sensitivity of the reagents, particularly when the explosive materials may contain plasticizers (this applies especially in the case of reagents A and B). Additionally, in the case of reagent C, the DMSO increases the viscosity of the liquid phase and prevents agglomeration of the zinc grains. Further, in the case of reagent D, the DMSO moderates the aggressive and corrosive character of the highly acid solution. Moreover, the DMSO being water-miscible, does not detract from the chemical reactions in question, which in practice are effected in aqueous media. However, it is contemplated that other solvents such as dimethylformamide, dimethylacetamide, hexamethylphosphoramide or N-methylpyrrolidone, in particular, might be considered as possible alternative or additional solvents, in the present context.

Reagent A (for nitroaromatics)

Working under the conditions described above, sulfanilamide (20 g) is dissolved in a magnetically stirred mixture of DMSO (700 ml) and 5% KOH in 40:60 methanol/isopropyl alcohol (300 ml); if a small amount of residue remains, the liquid phase may be decanted or filtered, prior to transfer to storage and filling ampoules. This reagent gives a pink to red or violet-red coloration with nitroaromatics such as TNT, DNT, TNB or tetryl (sensitivity to about $5 \times 10^{-4}$ mg), and a yellow color with picric acid or its salts (sensitivity $10^{-3}$ mg).

Reagent B (for organic esters of nitric acid and nitramines)

Working under the conditions described above, N-(1-naphthyl)ethylenediamine (3 g) is added to a magnetically stirred mixture of 85% phosphoric acid (100 ml) and twice-distilled water (900 mi), followed by hydrazinc sulfate (5 g) and sodium thiosulfate pentahydrate (0.5 g). (It is presently contemplated that metabisulfite or ascorbic acid might be used additionally or in the alternative, as nitrate to nitrite ion reducing agents). Active carbon (1 g) is added and stirring is continued for a Further 15 minutes, after which the mixture is filtered, prior to transfer to storage and filling ampoules. This reagent gives a violet to red coloration with nitrate ester or nitramine explosives such as dynamite, HMX, smokeless powder, nitroglycerine, PETN, RDX, C4 and Semtex. The sensitivity of this test is in the range $10^{-4}$ to $10^{-5}$ mg.

Reagent C (for inorganic nitrates)

To a mixture of magnetically stirred DMSO (600 ml) and isopropyl alcohol (400 ml), there is added zinc powder (20 g) which had previously been finely ground in a mortar. Stirring is stopped after 10 minutes. After allowing to stand for a further 10 minutes, the desired supernatant, which is a turbid grey liquid, is decanted from the residue of coarse zinc particles, and poured into a storage vessel prior to being used for filling ampoules. The thus-prepared emulsion containing zinc is very stable to light and under normal conditions; the ampoules do not need to be colored. This reagent gives a violet-red or red coloration with nitrates and is sensitive to as little as $10^{-5}$ mg of nitrate.

Reagent D (for chlorates or bromates)

A liquid mixture is first prepared by carefully adding 95% sulfuric acid (400 ml) to a mixture of DMSO (90 ml), ethanol (100 ml) and water (500 ml). Aniline sulfate (23 g) is then added with stirring to the liquid mixture until a homogeneous solution is obtained. The thus-prepared reagent is poured into a storage vessel prior to being used for Filling ampoules. It is very stable to light and under normal conditions; the ampoules do not need to be colored. This reagent gives a strong blue coloration with chlorates within 10–20 seconds, which fades on standing; it is sensitive to as little as $2 \times 10^{-2}$ mg of chlorate. A bluish-pink color is obtained in the presence of bromate; perchlorate does not give a positive reaction.

The invention will now be illustrated by the following non-limiting example.

EXAMPLE

FIG. 1 depicts a particular embodiment of a kit in accordance with the present invention (a suggested marketing name for which is "ETK-plus"), in which for the sake of illustration the various components are shown outside the container, which in the drawing is attache case 2. The items shown in FIG. 1 are not necessarily drawn to scale. Reagents A, B, C and D are contained in sealed ampoules (illustratively 12) within each of plastic tubes 4, 6, 8 and 10, respectively. Illustratively, each tube may contain two ampoules containing an identical reagent. These plastic tubes, which may be made from any suitable material known in the art, e.g. low density polyethylene, of thickness of 0.8 mm. for example, are conveniently tapered at one end, as shown, in a conventional manner, in order to permit the reagent solutions to be dispensed dropwise, when required, and most preferably contain replaceable caps, such as screw caps, in order to prolong the life of the reagents. The plastic tubes may be colored coded for ready identification.

The illustrated kit contains two kinds of disks used For collecting the samples to be tested, a thin absorbent paper disk 14, stored until required in jar 16, for wiping suspected surfaces and a disk of absorbent paper 20 compressed between a plastic disc 18 and a plastic ring 19 (and stored in tube 22) whereby the finger tips of suspected persons can be wiped on disk 20, with application of appropriate pressure, without contamination by the operator. Reference numeral 24 denotes a "nutracket" type device for breaking open the ampoules 12 as required.

While the various components of the kit, and their container, can evidently be of any convenient size, exemplary approximate dimensions, in a particular embodiment, may be as follows:

| | |
|---|---|
| attache case 2 | 23 × 18.5 × 4.5 cm |
| tubes 4, 6, 8, 10 | 12 cm (length to tip of cap) × 4-2.5 cm |
| ampoules 12 | 5 × 0.9-0.8 cm |
| disk 14 | 4 cm diameter |
| storage jar 16 | 3.3 cm (height) × 5.5 cm (diameter) |
| disk assembly 18-19-20 | 2.5 cm (diameter) × 2 mm (thickness) |
| storage tube 22 | 8.5 cm (length) × 3.5 cm (diameter) |
| "nutcracker" device 24 | 12.5 × 1 × 1 cm (dimensions of each arm) |

In operation, disks 14 and/or 20, as appropriate, are removed from their respective storage containers 16, 22 (after removing respective closures 26,28) and wiped over the surfaces (or the skin of persons) suspected of being in contact with explosives. Alternatively, a minute sample of dust or other suspect substance, if available, may be place on the disks. Note that rapid replacement of the caps of the plastic tubes will prolong the life of reagents A and B, once the ampoules have been broken. The following test procedure is then carried out:

(a) The suspect sample is treated with one drop reagent A after breaking the ampoule within tube 4; a pink to red or violet-red coloration indicates the presence of an explosive from group I such as TNT (violet-red). DNT, TNB or tetryl (red), but picric acid or salts thereof give a yellow color.

(b) If no coloration is obtained in (a), the same suspect sample on the same disk is then treated with one drop reagent B after breaking the ampoule within tube 6; a violet to red coloration indicates the presence of an explosive from group II such as dynamite, HMX, smokeless powder, nitroglycerine, PETN (violet), RDX (violet), C4 and Semtex (violet).

(c) If no coloration is obtained in (a) or (b), reagent C is used, after first shaking the ampoule thoroughly. The same suspect sample on the same disk is then treated with one drop reagent C after breaking the ampoule within tube 8; a red or violet-red coloration indicates the presence of an explosive from group III e.g. an improvised explosive containing an inorganic nitrate.

(d) If no coloration is obtained in any of (a), (b) and (c), a new sample on a different disk 14 or 20 is provided, and this is treated with to drops reagent D after breaking the ampoule within tube 10; a blue or bluish-pink coloration which develops within about 20 seconds indicates the presence of an explosive from group IV e.g. as an improvised explosive containing chlorate or bromate. Caution: reagent D is strongly acidic and corrosive and should be handled with care.

The kits may contain additionally samples of test paper discs containing respective samples of nitroaromatic and nitrate ester or nitramine explosives, for checking on the viability of reagents A and B after the ampoules have been broken.

UTILITY AND ADVANTAGES OF THE INVENTION

The method and kit of the invention provide for the rapid detection of explosives in a manner which is sensitive, simple, precise and reliable. The class of explosive and in certain cases the actual identity of the explosive can be determined, and the invention allows antiterrorist personnel to detect persons who have handled explosives, as well as surfaces having had contact with explosives such as clothes, luggage, door handles and car surfaces. The kit need not weigh more than about 400 g, and may have a dimensions of (e.g.) 23×18.5×4.5 cm.

The reagents used in the method and kit of the invention have a shelf life of at least one year at 25° C. and for a longer period of time under refrigeration at 4° C. If the appropriate care is taken in the manufacture and initial storage of reagents A and B, they may be used up to 2 weeks from when the ampoules are crushed (if stored at 25° C.), whereas in a previous version they could not have been used more than 24 hours after breaking the ampoules, so that in practice these reagents could only be used for a single operation. In the previous version, reagent C was a solid, and the liquid phase reagent now provided in its place gives better contact with the suspect sample and is therefore to be regarded as more reliable. The present invention, which in a particular embodiment includes reagent D, now allows For the detection of a separate group of materials which can be used especially in improvised explosives, namely, chlorates and bromates.

While the present invention has been particularly described with respect to its presently preferred embodiments, it will be appreciated by skilled persons that many modifications and variations may be made. Merely by way of example, the reagents could be microencapsulated instead of being contained in ampoules, or the reagents could be contained in sprays, instead of in the form of ampoules within plastic tubes as in the presently illustrated embodiment. (It is presently believed that the presently described embodiment is preferable as being more environment- and user-friendly than sprays, but this does not mean necessarily that in certain contexts the sprays would not be commercially viable). Consequently, it will be appreciated that the invention is not to be construed as restricted to the particularly described embodiments, rather regard will be had to the concept, spirit and scope of the invention, in view of the present disclosure and the claims which follow.

I claim:

1. In a test kit for detecting explosives, which kit contains reagents for detecting inorganic nitrates, chlorates and bromates, and reagents for detecting explosive substances selected from nitroaromatics, organic nitrates and nitramines, the improvement which comprises incorporating in said test kit at least one of the following two items:

an inorganic nitrate detecting reagent which comprises an admixture of zinc powder with liquid comprising at least one water-miscible organic solvent and which on shaking gives a suspension of said zinc powder therein, wherein said admixture is contained in dispensing means; and a chlorate or bromate detecting reagent which comprises an aniline salt in a homogeneous acidic solution including at least one water-miscible organic solvent, wherein said acidic solution is contained in dispensing means.

2. A test kit according to claim 1, wherein said strongly acidic solution comprises an oxyacid and contains also at least one water-miscible alcohol and at least one other water-miscible organic solvent.

3. A test kit according to claim 2, wherein said acidic solution comprises sulfuric acid and contains also ethanol and dimethyl sulfoxide.

4. A test kit according to claim 1, wherein said liquid contains at least one water-miscible alcohol and at least one other water-miscible organic solvent.

5. A test kit according to claim 4, wherein said liquid contains dimethyl sulfoxide and at least one alcohol selected from methyl alcohol and isopropyl alcohol.

6. A test kit according to claim 2, wherein said liquid contains at least one water-miscible alcohol and at least one other water-miscible organic solvent.

7. A test kit according to claim 6, wherein said liquid contains dimethyl sulfoxide and at least one alcohol selected from methyl alcohol and isopropyl alcohol.

8. A test kit according to claim 1, wherein each of said dispensing means effects a spray.

9. A test kit according to claim 8, wherein said admixture and said acidic solution are contained in separate sealed breakable ampoules which are enclosed in plastic tubes, said tubes allowing dropwise dispensing of the contents of the ampoules when these are broken, thus releasing said contents into said tubes.

10. In a test kit for detecting explosives, which kit contains reagents for detecting inorganic nitrates, chlorates and bromates, and reagents for detecting explosive substances selected from nitroaromatics, organic nitrates and nitramines, the improvement which comprises incorporating in said test kit at least one of the following two items:

an inorganic nitrate detecting reagent which comprises an admixture of zinc powder with liquid comprising at least one water-miscible organic solvent selected from the group consisting of dimethyl sulfoxide, dimethylformamide, dimethylacetamide, hexamethylphosphoramide and N-methylpyrrolidone, and which on shaking gives a suspension of said zinc powder therein, wherein said admixture is contained in dispensing means; and a chlorate or bromate detecting reagent which comprises an aniline salt in a homogeneous acidic solution including at least one water-miscible organic solvent selected from the group consisting of dimethyl sulfoxide, dimethylformamide, dimethylacetamide, hexamethylphosphoramide and N-methylpyrrolidone, wherein said acidic solution is contained in dispensing means.

11. A test kit according to claim 10, wherein said admixture and said acidic solution are contained in separate sealed breakable ampoules which are enclosed in plastic tubes, said tubes allowing dropwise dispensing of the contents of the ampoules when these are broken, thus releasing said contents into said tubes.

12. A test kit according to claim 10, wherein each of said dispensing means effects a spray.

13. A reagent kit for detecting explosives, which comprises a reagent selected from the group consisting of the following two reagents:

an inorganic nitrate explosive detecting reagent which comprises an admixture of zinc powder with liquid comprising at least one water-miscible organic solvent and which on shaking gives a suspension of said zinc powder therein, wherein said admixture is contained in dispensing means; and a chlorate or bromate explosive detecting reagent which comprises an aniline salt in a homogeneous acidic solution including at least one water-miscible organic solvent, wherein said acidic solution is contained in dispensing means.

14. Reagent kit according to claim 13, wherein said acidic solution comprises an oxyacid and contains also at least one water-miscible alcohol and at least one other water-miscible organic solvent.

15. Reagent kit according to claim 14, wherein said liquid contains at least one water-miscible alcohol and at least one other water-miscible organic solvent.

16. Reagent kit according to claim 15, wherein said liquid contains dimethyl sulfoxide and at least one alcohol selected from methyl alcohol and isopropyl alcohol.

17. Reagent kit according to claim 14, wherein said acidic solution comprises sulfuric acid and contains also ethanol and dimethyl sulfoxide.

18. Reagent kit according to claim 13, wherein said liquid contains at least one water-miscible alcohol and at least one other water-miscible organic solvent.

19. Reagent kit according to claim 18, wherein said liquid contains dimethyl sulfoxide and at least one alcohol selected from methyl alcohol and isopropyl alcohol.

20. Reagent kit according to claim 13, wherein said admixture and said acidic solution are contained in separate sealed breakable ampoules which are enclosed in plastic tubes, said tubes allowing dropwise dispensing of the contents of the ampoules when these are broken, thus releasing said contents into said tubes.

21. A reagent kit according to claim 13, wherein each of said dispensing means effects a spray.

22. A reagent kit for detecting explosives, which comprises a reagent selected from the group consisting of the following two reagents:

an inorganic nitrate explosive detecting reagent which comprises an admixture of zinc powder with liquid comprising at least one water-miscible organic solvent selected from the group consisting of dimethyl sulfoxide, dimethylformamide, dimethylacetamide, hexamethylphosphoramide and N-methylpyrrolidone, and which on shaking gives a suspension of said zinc powder therein, wherein said admixture is contained in dispensing means; and a chlorate or bromate explosive detecting reagent which comprises an aniline salt in a homogeneous acidic solution including at least one water-miscible organic solvent selected from the group consisting of dimethyl sulfoxide, dimethylformamide, dimethylacetamide, hexamethylphosphoramide and N-methylpyrrolidone, wherein said acidic solution is contained in dispensing means.

23. Reagent kit according to claim 22, wherein said admixture and said acidic solution are contained in separate sealed breakable ampoules which are enclosed in plastic tubes, said tubes allowing dropwise dispensing of the contents of the ampoules when these are broken, thus releasing said contents into said tubes.

24. A reagent kit according to claim 22, wherein each of said dispensing means effects a spray.

* * * * *